(12) United States Patent
Shams

(10) Patent No.: US 8,374,798 B2
(45) Date of Patent: Feb. 12, 2013

(54) APPARATUS, METHOD, AND COMPUTER PROGRAM PRODUCT FOR DETERMINING GENE FUNCTION AND FUNCTIONAL GROUPS USING CHROMOSOMAL DISTRIBUTION PATTERNS

(76) Inventor: Soheil Shams, Manhattan Beach, CA (US)

( * ) Notice: Subject to any disclaimer, the term of this patent is extended or adjusted under 35 U.S.C. 154(b) by 275 days.

(21) Appl. No.: 12/661,920

(22) Filed: Mar. 26, 2010

(65) Prior Publication Data

US 2010/0191473 A1 Jul. 29, 2010

Related U.S. Application Data

(63) Continuation-in-part of application No. 10/609,137, filed on Jun. 26, 2003, now Pat. No. 7,689,365.

(60) Provisional application No. 60/392,150, filed on Jun. 26, 2002.

(51) Int. Cl.
*G06F 19/00* (2011.01)
*G06F 15/00* (2006.01)
*G11C 17/00* (2006.01)

(52) U.S. Cl. .................. 702/20; 700/1; 365/94

(58) Field of Classification Search .......... None
See application file for complete search history.

(56) References Cited

U.S. PATENT DOCUMENTS 6,950,755 B2   9/2005  Stahl
7,689,365 B2 * 3/2010  Shams ............................ 702/19

OTHER PUBLICATIONS

Caron et al. The Human Transcriptome Map: Clustering of Highly Expressed Genes in Chromosomal Domains Science vol. 291, pp. 1289-1292 and Supplementary Material (2001).*
Kanehisa et al. DEGG: Kyoto Encyclopedia of Genes and Genomes Nucleic Acids Research vol. 28, pp. 27-30 (2000).*
Paul T. Spellman and Gerald M. Rubin, "Evidence for large domains of similarly expressed genes in the *Drosophila* genome," Journal of Biology 2002, vol. I, Issue I, Article 5, BioMed Central, pp. 5.1-5.8.

* cited by examiner

Primary Examiner — John S Brusca

(57) ABSTRACT

A method, apparatus, and computer program product for analyzing gene expressions is presented. An operation is performed for determining a gene expression pattern for a condition, wherein the gene expression pattern comprises a gene expression. Next, a spatial-expression pattern is formed by selecting a chromosomal region having an exon; and associating the gene expression within the gene expression pattern with its corresponding exon. A further operation may be performed, where in the forming of the spatial-expression pattern, a spatial-expression pattern signal is created as a representation of the spatial-expression pattern. The magnitude of the spatial-expression pattern signal at any point is determined by an expression level of the corresponding exon. Spatial patterns may be identified in the signal by means of various signal processing techniques such as Fourier or Wavelet transforms. Also, multiple regions and/or conditions may be tested and their reaction patterns compared to determine related genetic regions.

4 Claims, 8 Drawing Sheets

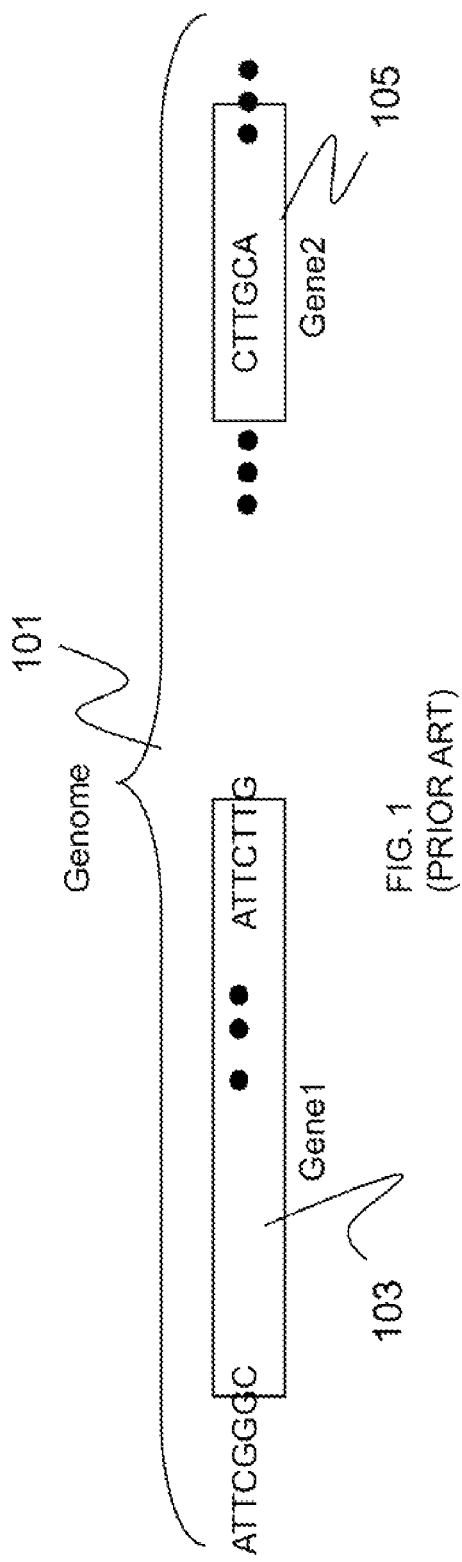

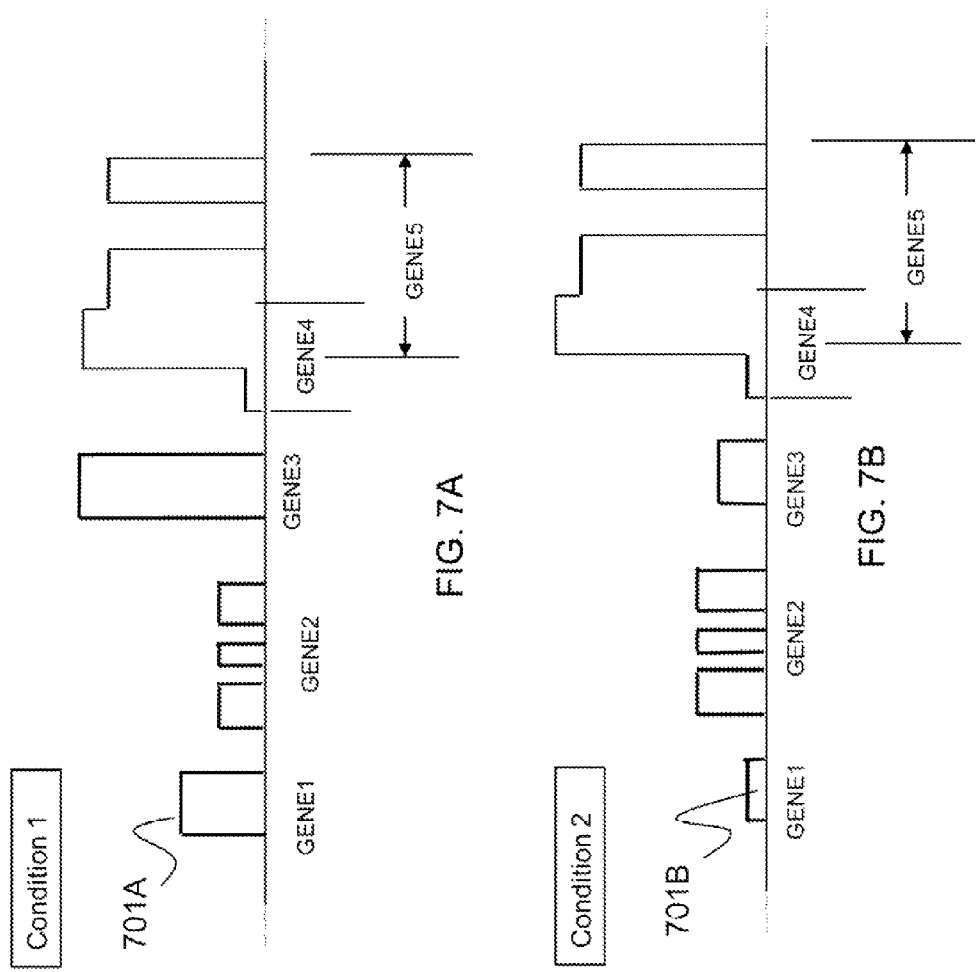

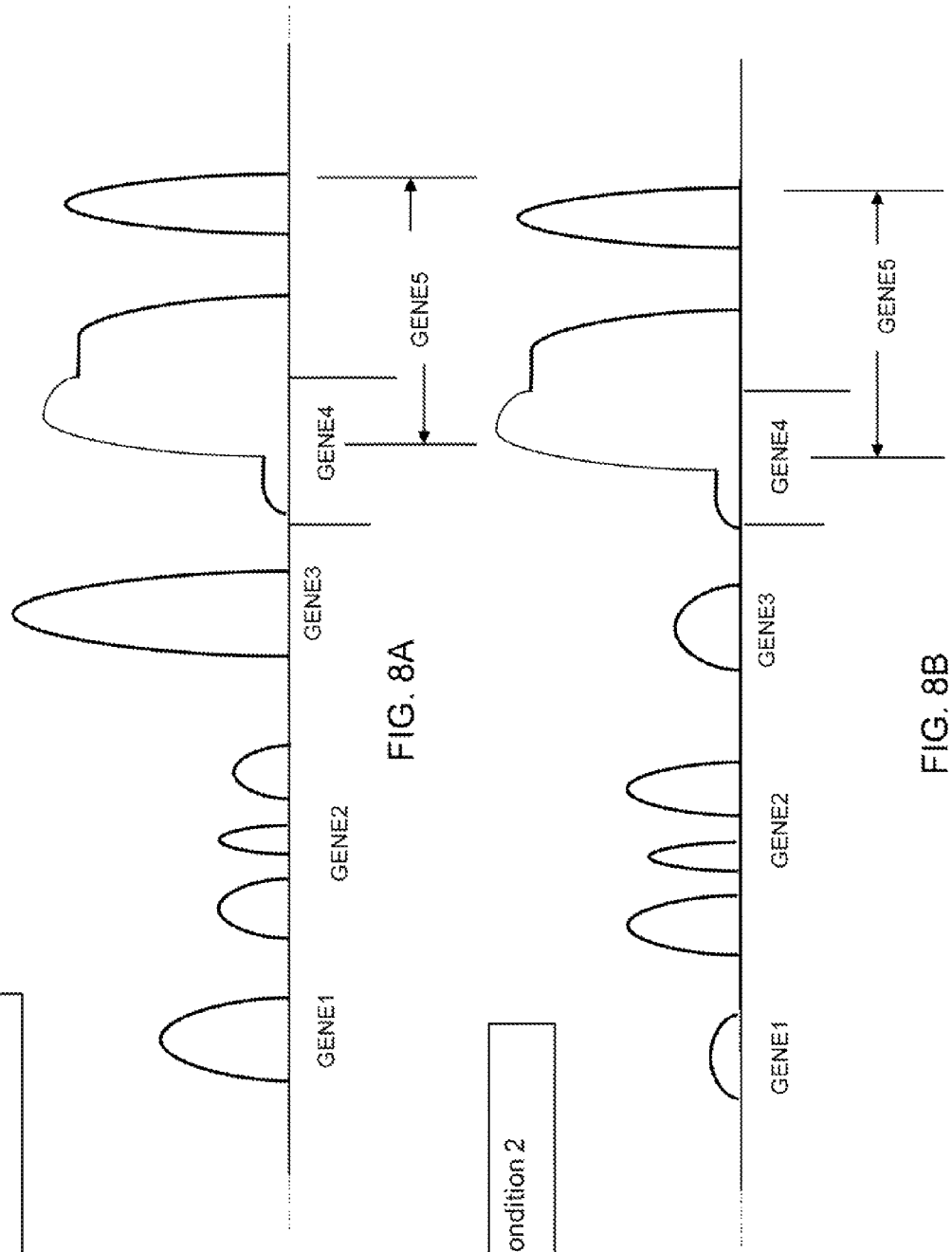

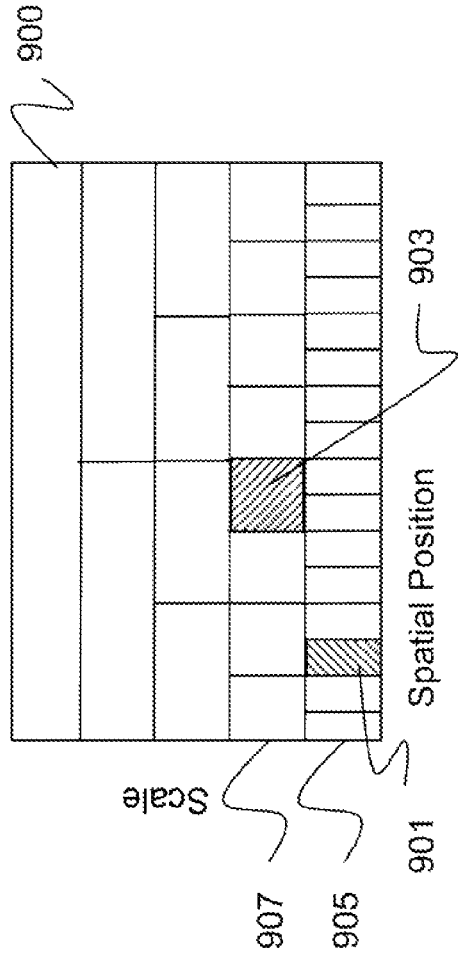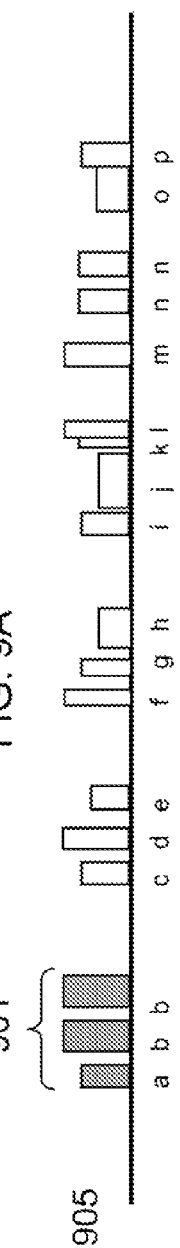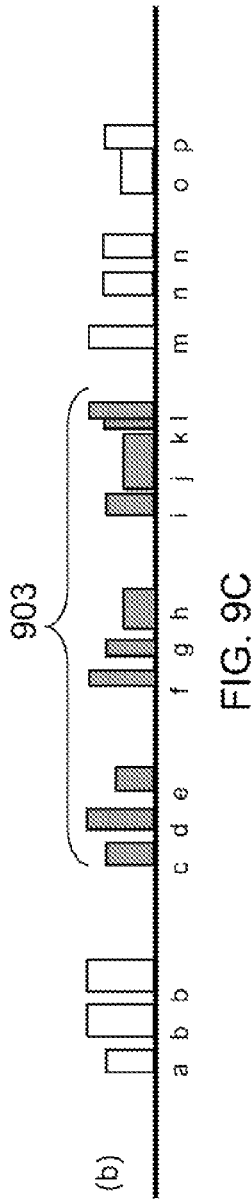
FIG. 9A
FIG. 9B
FIG. 9C

APPARATUS, METHOD, AND COMPUTER PROGRAM PRODUCT FOR DETERMINING GENE FUNCTION AND FUNCTIONAL GROUPS USING CHROMOSOMAL DISTRIBUTION PATTERNS

PRIORITY CLAIM

This is a Continuation-in-Part Application of U.S. Non-Provisional application Ser. No. 10/609,137, filed on Jun. 26, 2003, entitled, "Apparatus, Method, and Computer Program Product for Determining Gene Function and Functional Groups Using Chromosomal Distribution Patterns," which issues as U.S. Pat. No. 7,689,365 on Mar. 30, 2010, which claimed priority to U.S. Provisional Application No. 60/392,150, filed on Jun. 26, 2002, entitled, "Representation and Comparison of Gene Expression Patterns Using Wavelet Signal Processing," now expired.

BACKGROUND (1) Technical Field

The present invention relates to creating and analyzing spatial-expression patterns, wherein the spatial-expression pattern involves integrating the expression data with the spatial distribution of expression information.

(2) Discussion

The bioinformatics field, which, in a broad sense, includes any use of computers in solving information problems in the life sciences, and more particularly, the creation and use of extensive electronic databases on genomes, proteomes, etc., is currently in a stage of rapid growth.

In order to understand some of the concepts in the bioinformatics field, it is important to understand some of the basic principals of cells. A cell relies on proteins for a variety of its functions. Producing energy, biosynthesizing all component macromolecules, maintaining cellular architecture, and acting upon intra- and extra-cellular stimuli are all protein dependent activities. Almost every cell within an organism contains the information necessary to produce the entire repertoire of proteins that the organism can specify. This information is stored as genes within the organism's DNA genome. Different organisms have different numbers of genes to define them. The number of human genes, for example, is estimated to be approximately 25,000.

Genetic information of all life forms is encoded by the four basic nucleotides, denoted by symbols A, G, C, and T. The make up of all life forms is determined by the sequence of these nucleotides. DNA is the molecule that encodes this sequence of nucleotides. The DNA molecule usually contains a large number of genes. Each gene provides biochemical instructions on how to construct a particular protein. The one-to-one nature of one gene creating one protein has been recently changed. In some cases multiple genes are required to create a single protein and commonly multiple proteins can be produced through alternative splicing and post-transcriptional modification of a single gene. Recently, much attention has also been directed at "Copy Number Variations" or "Copy Number Polymorphisms". Scientists have determined that genomes of different people have small deletions and insertions of sequences of various sizes scattered through the DNA. Much of these so called CNVs or CNPs do not produce obvious phenotypes. However, it is suspected that such changes can create pre-disposition to various conditions. These CNVs can be in any area of the genome including between genes, within the intronic areas of genes or even in Exons. An example of a genome is depicted in FIG. 1, wherein the genes 103, 105 are defined as segments of nucleotide sequence on the DNA genome 101. As depicted in FIG. 1, the letter "N" represents any of the four DNA nucleotides: "A," "C," "G," or "T."

Only a portion of the genome is composed of genes, and the set of genes expressed as proteins varies between cell types. Some of the proteins present in a single cell are likely to be present in all cells because they serve functions required in every type of cell. These proteins can be thought of as "house-keeping" proteins. Other proteins serve specialized functions that are only required in particular cell types. Such proteins are generally produced only in limited types of cells. Given that a large part of a cell's specific functionality is determined by the genes that it is expressing, it is logical that transcription, the first step in the process of converting the genetic information stored in an organism's genome into protein, would be highly regulated by the control network that coordinates and directs cellular activity.

Genes are activated, or expressed, in a very specific fashion and to a specific level at any given moment in time to achieve a desired state. The regulation of transcription is readily observed in studies that scrutinize activities evident in cells configuring themselves for a particular function (specialization into a muscle cell) or state (active multiplication or quiescence). As cells alter their state, coordinate transcription of the protein sets required for the change of state can be observed. As a window both on cell status and the system controlling the cell, detailed, global knowledge of the transcriptional state could provide a broad spectrum of information useful to biologists. For instance, knowledge of when and in what types of cell the protein product of a gene of unknown function is expressed would provide useful clues as to the likely function of that gene. Furthermore, determining gene expression patterns in normal cells could provide detailed knowledge of how the control system achieves the highly coordinated activation and deactivation required to develop and differentiate a single fertilized egg into a mature organism. Also, comparing gene expression patterns in normal and pathological cells could provide useful diagnostic "fingerprints" and help identify aberrant functions that would be reasonable target for therapeutic intervention.

The current approaches in studying gene expression patterns attempt at understanding the differences in expression patterns of genes in different conditions (either a pair of conditions or a series of conditions) by comparing the level of expression of various genes one by one. FIG. 2 illustrates a simplified example where two different gene expression patterns 201, 203, each being composed of five distinct genes 205-209 are compared. Assume that Condition1 pattern 201 is for a healthy cell and Condition2 pattern 203 is for a diseased cell. Using an arbitrary expression scale of zero to ten, the example matrix of expression values is constructed as shown in FIG. 2.

Using the matrix of FIG. 2, the typical approach would compare the genes one by one and draw conclusions such as there are no significant differences in Gene4 208 so it probably does not contribute to differences observed in Condition1 201 and Condition2 203. However, Gene3 207 exhibits a large difference and might indicate a gene having some relation to the observed differences between Condition1 201 and Condition2 203. The common measures used to calculate the difference between Condition1 201 and Condition2 203 is to take a difference or ratio between the expression values gene by gene. For example, the Euclidean distance or the Pearson correlation value between the two expression vectors may be calculated.

These prior art approaches do not take into account a very important piece of information, the spatial distribution of genes, or the sequence of nucleotides, along the genome. The observation of the presence of extensive number of copy number changes in the genome (effecting the local position of genes) is further evidence in the need to look and process of the genome from a spatial arrangement perspective. Thus, what is needed is an apparatus, method and computer program product which takes into account not only the expression levels of the genes but also their spatial distribution.

SUMMARY OF THE INVENTION

A method, apparatus, and computer program product for analyzing gene expressions are presented. In this section, operations are presented that demonstrate various aspects of the invention. Although presented as "acts," the operations described present a descriptive overview of the functions and parts of the apparatus and computer program product as well as the method.

In a first aspect, an operation of determining a first gene expression pattern for a first condition is performed, wherein the first gene expression pattern comprises a gene expression. Next, a spatial-expression pattern is formed by selecting a chromosomal region having an exon; and associating the gene expression within the first gene expression pattern with its corresponding exon.

In another aspect, the act of forming the first spatial-expression pattern further comprises an act of creating a first spatial-expression pattern signal wherein the first spatial-expression pattern signal is a representation of the first spatial-expression pattern where a magnitude of the first spatial-expression pattern signal at any point is determined by an expression level of the corresponding exon.

In still another aspect, the magnitude of the first spatial-expression pattern signal at points spanning the chromosomal region are a function of the expression level of an exon at corresponding positions in the chromosomal region.

In a further aspect, an operation is performed for identifying first regular spatial patterns in the first spatial-expression pattern signal.

In a yet further aspect, the act of identifying first regular spatial patterns in the first spatial-expression pattern signal is performed through the use of Fourier transform signal processing. In this case, a group of genes contributing to local maximum points of the generated Fourier transform spectrum may be identified.

In another variation of this aspect, the act of identifying first regular spatial patterns in the first spatial-expression pattern signal is performed through the use of Wavelet transform signal processing. In this case, groups of genes may be identified by their contribution to local maximum points of the generated Wavelet transformed signal at different scales and positions.

In a still further aspect, the act of identifying first regular spatial patterns in the first spatial-expression pattern signal identifies a set of genes.

In yet another aspect, the act of identifying first regular spatial patterns in the first spatial-expression pattern signal identifies a set of genes which participate in a common biological process or function.

In another aspect, the invention further comprises an operation of determining a second gene expression pattern for a second condition, wherein the second gene expression pattern comprises a gene expression. Also, a second spatial-expression pattern is formed by selecting a chromosomal region having an exon; and associating a gene expression within the second gene expression pattern with its corresponding exon.

In an additional aspect, operations of identifying first regular spatial patterns in the first spatial-expression pattern signal; identifying second regular spatial patterns in the second spatial-expression pattern signal; and comparing the first and second regular spatial patterns are performed.

In yet another aspect, the steps of determining a gene expression pattern and forming a spatial-expression pattern signal may be repeated for any number of gene expression patterns. All spatial-expression pattern signals thus formed may be compared, and the comparing may involve clustering all of the formed spatial-expression signals.

In a further aspect, gene groups contributing to differences in significant changes in the first and second regular spatial-expression pattern signals may be identified.

In a still further aspect, the chromosomal region is an entire chromosome.

In another aspect, the first spatial-expression pattern and the second-expression pattern are selected from different chromosomes.

In still another aspect, the first spatial-expression and the second-expression pattern are selected from different genomes.

The above-mentioned aspects of the present invention will be presented in much greater detail in the description and drawings that follow in a manner intended to permit one of skill in the art to practice all aspects of the invention described and claimed herein.

BRIEF DESCRIPTION OF THE DRAWINGS

The objects, features and advantages of the present invention will be apparent from the following detailed descriptions of the preferred embodiment of the invention in conjunction with reference to the following drawings where:

FIG. 1 is a prior art depiction of genes within a genome;

FIG. 2 is a prior art matrix of expression values for several genes for two different conditions;

FIG. 7A depicts a spatial-expression pattern signal for Condition1 generated from the spatial-expression pattern of FIG. 5 and the gene expression data in FIG. 2;

FIG. 7B depicts a spatial-expression pattern signal for Condition2 generated from the spatial-expression pattern of FIG. 5 and the gene expression data in FIG. 2;

FIG. 8A depicts another spatial-expression pattern signal for Condition1 generated from the spatial-expression pattern of FIG. 5 and the gene expression data in FIG. 2;

FIG. 8B depicts another spatial-expression pattern signal generated for Condition2 from the spatial-expression pattern of FIG. 5 and the gene expression data in FIG. 2;

FIG. 9A depicts a wavelet transformation;

FIG. 9B is a detailed view of one of the information gathered from one of the peaks in the wavelet transformation of FIG. 9A; and FIG. 9C is a detailed view of information gathered from another of the peaks in the wavelet transformation of FIG. 9A.

DETAILED DESCRIPTION

Figure 3:
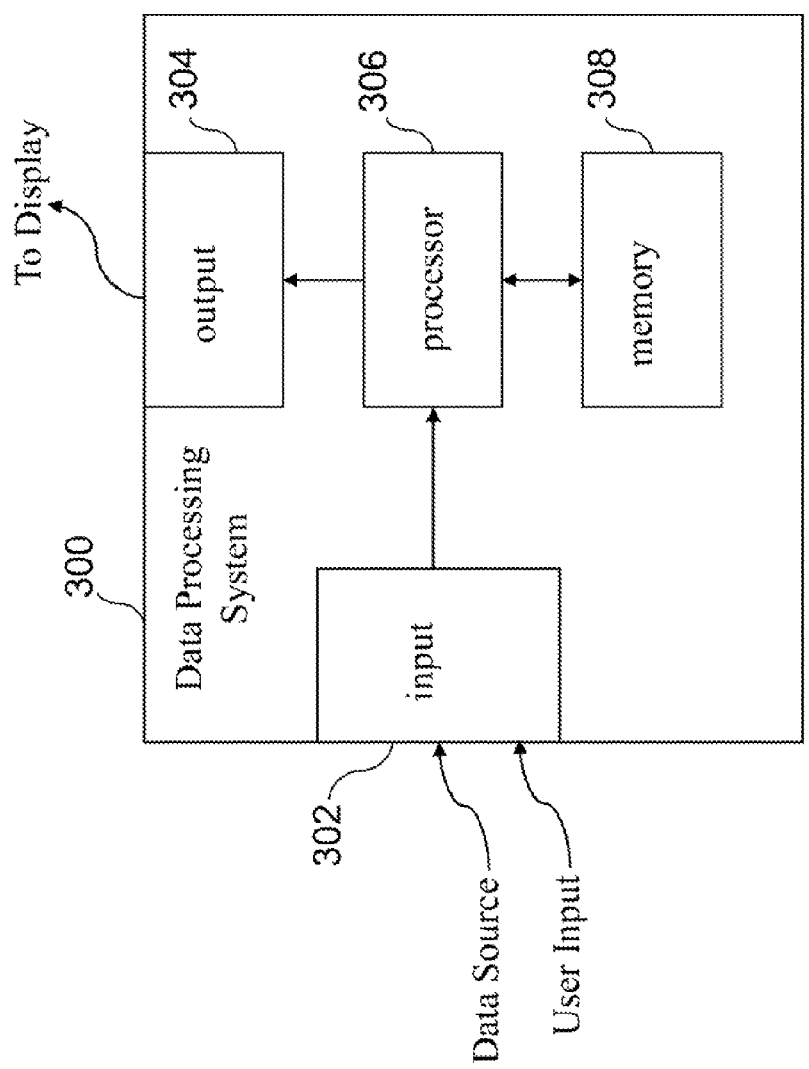
FIG. 3 is a block diagram depicting the components of a computer system used in the present invention.

The present invention relates to creating and analyzing spatial-expression patterns, wherein the spatial-expression pattern involves integrating the expression data with the spatial distribution of expression information. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In order to provide a working frame of reference, first a glossary of some of the terms used in the description and claims is given as a central resource for the reader. The glossary is intended to provide the reader with a "feel" for various terms as they are used in this disclosure, but is not intended to limit the scope of these terms. Rather, the scope of the terms is intended to be construed with reference to this disclosure as a whole and with respect to the claims below. Then, a brief introduction is provided in the form of a narrative description of the present invention to give a conceptual understanding prior to developing the specific details.

(1) Glossary

Before describing the specific details of the present invention, it is useful to provide a centralized location for various terms used herein and in the claims. The terms defined are as follows:

Means—The term "means" as used with respect to this invention generally indicates a set of operations to be performed on a computer. Non-limiting examples of "means" include computer program code (source or object code) and "hard-coded" electronics. The "means" may be stored in the memory of a computer or on a computer readable medium.

(2) Introduction

The present invention provides a mechanism for providing spatial-expression patterns where gene expressions are viewed based on their spatial frequency. To analyze these spatial-expression patterns the comparisons are based in a mixed scale/frequency space rather than the simple spatial (gene by gene) space. In order to achieve this goal, the expression patterns are overlaid on the physical location of genes along the chromosomes to create a spatial-expression pattern. These spatial-expression patterns are then analyzed. In one embodiment, spatial-expression pattern signals are formed based upon the spatial-expression patterns. This spatial-expression pattern signal may then be analyzed using a variety of signal processing techniques such as Fourier transform signal processing or Wavelet transform signal processing. This analysis may be used in identifying a set of genes which participate in a common biological process or function.

(3) Physical Embodiments of the Present Invention

The present invention has three principal "physical" embodiments. The first is an apparatus for obtaining and analyzing spatial-expression patterns, typically in the form of a computer system using software instructions. The instructions may also be in the form of a "hard-coded" instruction set. The second physical embodiment is a method, typically in the form of software, operated using a data processing system (computer). The third principal physical embodiment is a computer program product. The computer program product generally represents computer readable code stored on a computer readable medium such as an optical storage device, e.g., a compact disc (CD) or digital versatile disc (DVD), or a magnetic storage device such as a floppy disk or magnetic tape. Other, non-limiting examples of computer readable media include hard disks and flash-type memories. These embodiments will be described in more detail below.

A block diagram depicting the components of a computer system used in the present invention is provided in FIG. 3. The data processing system 300 comprises an input 302 for receiving gene expression patterns and their corresponding locating within a genome, from a data source. Note that the input 302 may include multiple "ports" for receiving data and user input. Typically, user input is received from traditional input/output devices such as a mouse, trackball, keyboard, light pen, etc., but may also be received from other means such as voice or gesture recognition for example. The output 304 is connected with the processor for providing output. Output to a user is preferably provided on a video display such as a computer screen, but may also be provided via printers or other means. Output may also be provided to other devices or other programs for use therein. The input 302 and the output 304 are both coupled with a processor 306, which may be a general-purpose computer processor or a specialized processor designed specifically for use with the present invention. The processor 306 is coupled with a memory 308 to permit storage of data and software to be manipulated by commands to the processor.

Figure 4:
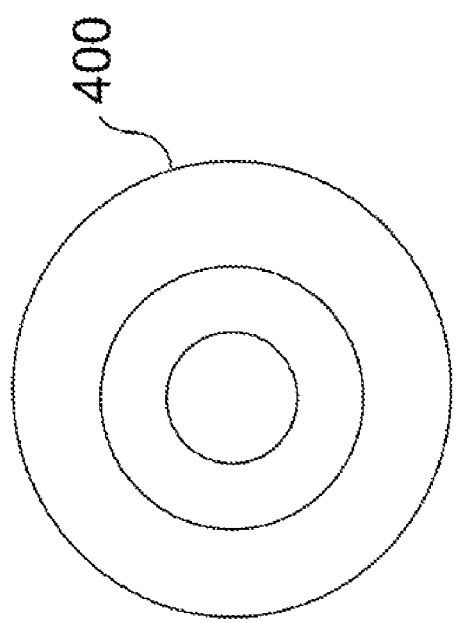
FIG. 4 is an illustrative diagram of a computer program product embodying the present invention.

An illustrative diagram of a computer program product embodying the present invention is depicted in FIG. 4. The computer program product 400 is depicted as an optical disk such as a CD or DVD. However, as mentioned previously, the computer program product generally represents computer readable code stored on any compatible computer readable medium.

(4) The Embodiments

Figure 5:
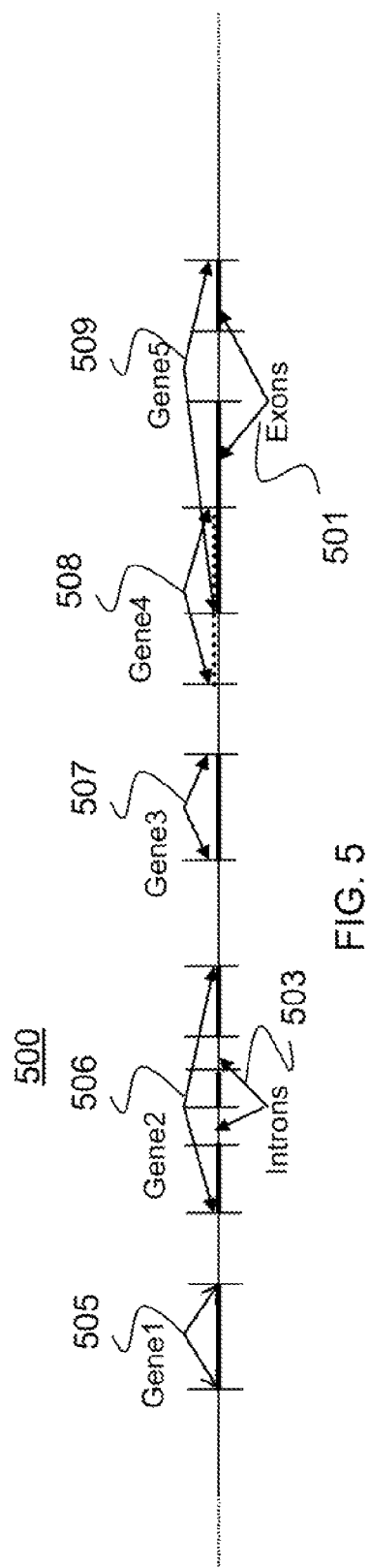
FIG. 5 depicts an exemplary gene structure 500 comprising of five genes 505-509.

The process for creation of the spatial-expression pattern involves integrating expression data with spatial distribution of expression information. It is assumed here that information about the specific genome of interest is available. Since no two genomes are identical, the physical position of each gene and its constituent exons must already been know. These positions should have taken into account any genomic changes due to copy number polymorphisms (e.g. insertions and deletions of segments of DNA) FIG. 5 depicts an exemplary gene structure 500 comprising of five genes 505-509. The gene's structure 500 contains two general types of areas, exons 501 and introns 503. The exon regions 501 of the gene structure 500 are also called the coding region and are the actual parts that are being expressed. The intron regions 503 are non-coding and are thus not expressed. In the framework described here, introns 503 play a key role by introducing specific spatial separation between exon regions 501 (i.e. coding regions).

As shown in FIG. 5, Gene1 505 and Gene3 507 are shown as having a continuous region without any introns 503 (this can be viewed as the gene having a single exon 501). On the other hand, Gene2 506 is made up of 3 exons 501 separated by two introns 503.

Figure 6:
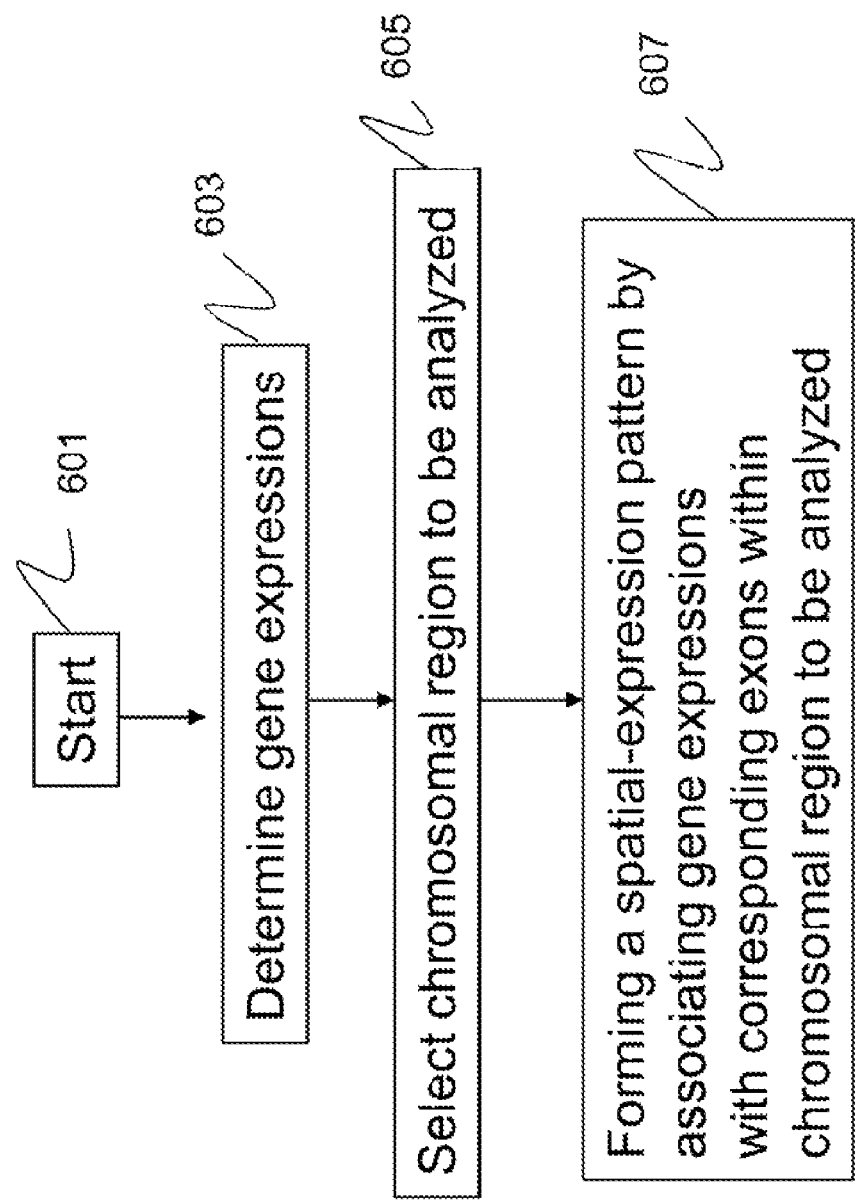
FIG. 6 outlines the acts involved in the creation of a spatial-expression pattern.

The process for creation of a spatial-expression pattern involves integrating the expression data with the spatial distribution of gene and the gene's interon/exon structure information. One skilled in the art will appreciate there are multiple ways of integrating this data. FIG. 6 outlines the acts involved in the creation of a spatial-expression pattern. First, after starting 601, the act of determining the gene expression pattern 603 is performed. This generally includes obtaining the measured gene expression values. Next, the act of selecting a chromosomal region to be analyzed 605 is performed. When creating the spatial-expression pattern, it is desirable that the expression values for the genes map to each exon. As will be described later, some exons might not be expressed at all or maybe expressed at different levels due to various splice variations. For simplicity, in the examples presented herein, it is assumed that all the exons making up a gene are expressed at the same level in the following examples. However, one skilled in the art will appreciate that the same concepts may be applied when the exons making up a gene are expressed at different levels. Finally, the act of forming a spatial-expression pattern 607 is performed by associating gene expressions with corresponding exons within the chromosomal region.

FIGS. 7A and 7B depict a spatial-expression pattern signal generated from the spatial-expression pattern of FIG. 5 and the gene expression data in FIG. 2. In this method for creating a spatial-expression pattern, a signal having a length equal to the length of a chromosomal region for which gene expression data is being analyzed is created. For every gene the start and stop position of the gene and its constituent exons is determined. At the specific chromosomal locations corresponding to each gene/exon, the magnitude of the spatial-expression pattern signal is set equal to the expression value of that gene or exon. For example, Gene1 in FIG. 2 has an expression value of 4 for Condition1 201 and an expression value of 1 for Condition2. This is reflected as Gene1 having a signal magnitude 701A, shown in FIG. 7A, greater than a signal magnitude 701B, shown in FIG. 7B. Further, as shown in FIGS. 7A and 7B, when two genes overlap, i.e. Gene4 and Gene5, the signal magnitude is the addition of the expression values for the overlapping signals.

FIGS. 8A and 8B depict another spatial-expression pattern signal generated from the spatial-expression pattern of FIG. 5 and the gene expression data in FIG. 2. In generating this spatial-expression pattern signal, a non-linear function is used to interpolate between the start and end points of the exons. For example, as shown in FIGS. 8A and 8B, a sine function can be used such that half the sine function cycle is mapped to the region between the start and stop part of each exon and the magnitude of the sine function is set to be equal to the expression value.

One skilled in the art will appreciate, that any function can be conceivably be used to interpolate between the start and end points of the exons as long as it integrates the expression values with their spatial distribution on the chromosome. As previously discussed, in creating the spatial-expression pattern signal, there can be regions of overlapping genes. Given the physical gene locations and the expression values, the expression values can be combined as can be seen for Gene 4 and one of the exons in Gene 5 in FIGS. 7A, 7B, 8A and 8B. One skilled in the art will appreciate that any method of combination may be used instead of addition as shown (for example, multiplication, log of the product, etc.). Furthermore, although FIGS. 7A, 7B, 8A and 8B show that all exons for a gene are at the level of the gene's expression value, one skilled in the art will appreciate that multiple splicing regions are possible where not all the exons in the gene are used during the transcription stage or in the post transcription stage. Therefore, it is desirable to create the signal based not on the overall gene's expression level but on each particular exon.

The spatial-expression pattern signals may be analyzed using many different signal processing methods in order to identify regular spatial patterns. In one embodiment, the gene expression patterns are analyzed as a spatial-expression pattern signal and the signal processing method preferably utilizes both the local expression values (gene by gene) as well as spatial frequency of gene expression patterns as laid down on the chromosome. The spatial structure of gene expression pattern contains valuable information, such as co-expressed genes separated by regular spatial intervals across the genome all participate in a common biological process. Therefore, signal processing methods are used to identify such groups of genes (co-expressed with a common regular spatial distribution).

Furthermore, signal processing methods may also be used to identify a meta-structure that can help in identification of a group of genes that are involved at different levels of biological complexity, from low level, very specific processes to higher-level complex biological processes. This information is embedded in a multi-scale fashion, wherein the very basic biological functions are found in groups of genes forming the highest spatial frequencies and the higher level functions are present at progressively lower spatial frequency distribution of gene groups. For example, a particular gene performs a very specific function. However, a group of genes located in close spatial proximity and forming a specific spatial frequency are involved in a higher level biological group and continuing up this way a group of group of genes with a particular spatial frequency would be responsible for an even higher function. Based on this structure, comparisons across different cell types and species can be made and will be discussed later.

One signal processing method that may be used is the Fourier transform (or the Fast Fourier Transform (FFT)/Discrete Fourier Transform (DFT)). The Fourier transform may be utilized to identify regular and repetitive patterns in the spatial-expression pattern signal. However, the Fourier transform assumes infinitely long extend in the time (or spatial) domain. If a Fourier transform is used the local maximum points of the generated Fourier transform spectrum will identify a group of genes that are working together.

Another approach is to use the short-time Fourier transform or the Wavelet transform. The Wavelet transform may be applied to spatial-expression pattern signals as formulated above in FIGS. 7A, 7B, 8A and 8B to uncover biological functions. In previous applications, expression patterns had been obtained from various sources across time, thus generating a time-varying signal for each gene. Signal processing approaches were used to identify temporal patterns. In contrast, the signal processing approaches herein are applied to spatial-expression pattern signals, not time-varying signals for each gene.

As shown in FIG. 9A, the wavelet transformation can be performed on each signal to create a 2-dimensional representation of the signal 900. One dimension will be the scale and the other spatial position. The value of the transformed signal 900 at each point in this two dimensional representation indicates the degree of the presence of a particular frequency at a particular position of the signal. The wavelet transform enables the evaluation of the features of the signal in a multi-resolution sense. This representation detects spatial frequencies at different locations and resolutions.

Many different kinds of information may be obtained by generating spatial-expression patterns and applying the wavelet processing methods for uncovering pattern. A few of these applications will be described below.

One application is the identification of gene groups. The typical approach in predicting a genes function using expression data is through the use of clustering or other similarity finding algorithms. The basis of these algorithms is to look at the expression values of a number of genes under a set of conditions. This is done by looking at each condition as having an expression vector where each element of this vector is a particular gene. Then a clustering algorithm, such as K-means, Self-Organizing Maps (SOM), or hierarchical, is applied to group similar conditions together as well as similar genes. By grouping genes that have similar expression values across the different set of conditions, a hypothesis may be formed that these genes might be related.

Using the wavelet approach described above, related genes are those genes that contribute high values in the 2-D transformed space. To recover the genes and the related genes, peaks in the transformed space can be identified, and based on the location of the peak and its associated scale (or spatial frequency), the genes and group of genes can be identified. Depending on the scale level of the peak, groups of varying size can be identified.

For example, the 2-D wavelet transformed signal 900, shown in FIG. 9A, shows two peaks 901, 903 of the many possible peaks. The lowest level 905 of the transformed signal 900 corresponds to the highest frequency. The peak 901 is associated to a set of three exons a, b, b as indicated in FIG. 9B. Other peaks at this level (not shown) would correspond to other similarly co-expressed genes with a similar spatial frequency located in other areas along the genome. Thus, the peak 901 at the lowest row 905 indicates a group of inter-related genes. In this case, genes "a" and "b" are grouped together.

Moving higher in the scale space, higher level groupings of genes and their relations are revealed. As shown in FIG. 9A, the next higher level 907 contains peak 903. As shown in FIG. 9C, peak 903 is a group of groups of genes all involved in a more complex biological process. In this case, genes "c", "d", "e", "f", "g", "h", "i", "j", "k", and "l" are grouped together.

Another application is the comparison of spatial-expression patterns between different conditions and association of genes and gene groups to biological functions. Using the wavelet transformed signals as "signature" pattern for gene expression under various conditions, and by comparing the transformed expression patterns between different conditions, similarities and differences between conditions can be identified. Various clustering or pattern recognition tools can be used to compare and contrast spatial-expression patterns in the wavelet transformed space. Instead of using the gene expression values as the basis of the comparison, the amplitude of the spatial-expression transformed signal is used. The differences in the spatial-expression transformed patterns between two conditions (e.g., healthy vs. diseased) will point to genes or gene groups that are involved with making the biological difference between the two conditions.

Another application is comparison of spatial-expression patterns between different cells and organisms. Since the high frequency peaks are associated with detailed specific biological functions, the lower frequency features can be used to detect and identify groups of genes involved with functions that are more basic (and universal) across different cell types and organisms (such as metabolism). Therefore, the low frequency patterns can be used in clustering and other pattern recognition approaches can be used for comparing similarity and differences between different cell types and organisms. For example, a specific low-frequency peak detected as being significant in one cell type can be used to identify groups of genes having the same frequency in spatial separation in another cell type or organism.

Another application is identification of potential drug targets. By understanding the global nature of gene expression (groups of genes), it will be possible to predict better drug targets by identifying genes located in particular locations on the chromosome that can have a significant effect on the peaks of the wavelet transformed signal. For example, genes that should be altered to change a spatial-expression transformed signal of a diseased cell to that of a normal cell can be easily identified.

One skilled in the art will appreciate that while the examples provided above are limited to only two conditions evaluated, the concepts disclosed herein may be applied to many conditions, resulting in the formation of many spatial-expression pattern signals which can then be analyzed. Further, the concepts disclosed herein may be applied to an entire chromosome. In addition, a portion of one chromosome may be compared to a portion of another chromosome using the disclosed techniques wherein a spatial-expression pattern of Condition 1 is from one chromosome and a spatial-expression pattern of Condition 2 is from a different chromosome. Further, the concepts disclosed here may be applied to different genomes. In this case, a spatial-expression pattern of Condition 1 may be from one genome while a spatial-expression pattern of Condition 2 is from another genome.

What is claimed is:

1. A computer implemented method of analyzing gene expressions, the method comprising an act of:
   causing a computer to execute instructions encoded upon a memory, such that upon execution, the computer performs operations of:
   determining a first gene expression pattern for a first condition, wherein the first gene expression pattern comprises a gene expression;
   forming a first spatial-expression pattern by;
   selecting a chromosomal region having an exon;
   associating the gene expression within the first gene expression pattern with its corresponding exon;
   wherein the act of forming the first spatial-expression pattern further comprises an act of creating a first spatial-expression pattern signal wherein the first spatial-expression pattern signal is a representation of the first spatial-expression pattern where a magnitude of the first spatial-expression pattern signal at any point is determined by an expression level of the corresponding exon;
   identifying first regular spatial patterns in the first spatial-expression pattern signal; and
   wherein
   the act of identifying first regular spatial patterns in the first spatial-expression pattern signal is performed through the use of Fourier transform signal processing.

2. The method of claim 1 further comprising an act of:
   identifying a group of genes contributing to local maximum points of the generated Fourier transform spectrum.

3. An apparatus for analyzing gene expressions, the apparatus comprising a computer system including a processor, a memory coupled with the processor, an input coupled with the processor for receiving input data, and an output coupled with the processor for outputting data, wherein the memory includes instructions encoded thereon, such that upon execution of the instructions, the computer system performs operations of:
   determining a first gene expression pattern for a first condition, wherein the first gene expression pattern comprises a gene expression;
   forming a first spatial-expression pattern by:
   selecting a chromosomal region having an exon; and
   associating the gene expression within the first gene expression pattern with its corresponding exon; and
   wherein forming the first spatial-expression pattern includes creating a first spatial-expression pattern signal wherein the first spatial-expression pattern signal is a representation of the first spatial-expression pattern where a magnitude of the first spatial-expression pattern signal at any point is determined by an expression level of the corresponding, exon;

identifying, first regular spatial patterns in the first spatial-expression pattern signal; and wherein identifying first regular spatial patterns in the first spatial-expression pattern signal is performed through the use of Fourier transform signal processing.

4. A computer program product for analyzing gene expressions, the computer program product comprising instructions, encoded in a non-transitory computer-readable medium, for causing a computer to perform operations of:

determining a first gene expression pattern for a first condition, wherein the first gene expression pattern comprises a gene expression;

forming a first spatial-expression pattern by;

selecting a chromosomal region haying an exon; and associating the gene expression within the first gene expression pattern with its corresponding exon; and wherein forming the first spatial-expression pattern includes creating a first spatial-expression pattern signal wherein the first spatial-expression pattern signal is a representation of the first spatial-expression pattern where a magnitude of the first spatial-expression pattern signal at any point is determined by an expression level of the corresponding exon;

identifying first regular spatial patterns in the first spatial-expression pattern signal; and wherein identifying first regular spatial patterns in the first spatial-expression pattern signal is performed through the use of Fourier transform signal processing.

* * * * *